(12) United States Patent
Davies

(10) Patent No.: US 8,329,741 B2
(45) Date of Patent: Dec. 11, 2012

(54) SUBSTITUTED PYRROLIDINE COMPOUNDS WITH CENTRAL NERVOUS SYSTEM ACTIVITY

(75) Inventor: Huw M. L. Davies, Duluth, GA (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 12/144,232

(22) Filed: Jun. 23, 2008

(65) Prior Publication Data

US 2009/0048329 A1    Feb. 19, 2009

Related U.S. Application Data

(60) Provisional application No. 60/945,746, filed on Jun. 22, 2007.

(51) Int. Cl.
*A61K 31/40* (2006.01)
*C07D 207/12* (2006.01)

(52) U.S. Cl. ........................ 514/424; 548/556

(58) Field of Classification Search .......................... None
See application file for complete search history.

(56) References Cited

U.S. PATENT DOCUMENTS

2005/0010049 A1    1/2005    Davies

FOREIGN PATENT DOCUMENTS

| FR | 2081433 | 12/1971 |
| WO | WO 2006/113937 A2 | 10/2006 |

OTHER PUBLICATIONS

Dorwald F. A. Side Reactions in Organic Synthesis, 2005, Wiley: VCH, Weinheim. Preface and Chap. 1 included.*
Kubinyi, ed. 3D QSAR in Drug Design: Ligand-Protein Interactions and Molecular Similarity, vol. 2-3, Springer, 1998, 800 pages.*
Davies et al., Bioorg. Med. Chem. Lett. 14 (2004) 1799-1802.*
Davies et al., JACS, 2003, 125, pp. 6462-6468.*
Davies et al.; New Strategic Reactions for Organic Synthesis: Catalytic Asymmetric C-H Activation alpha to Nitrogen as a Surrogate for the Mannich Reaction; Journal of the American Chemical Society, 2003, vol. 125, No. 21; pp. 6462-6468.
Agawa et al.; Reaction of Vinyl Sulphone with alpha-Metallated Nitriles; J.C.S. Perkin I, 1981; pp. 751-755.
NI, Aiwu., et al., Diversity Synthesis Using the Complimentary Reactivity of Rhodium(II)- and Palladium (II)-Catalyzed Reactions, Journal of Organic Chemistry, 2006, vol. 71, No. 15, pp. 5594-5598.
Davies, Huw M.L., et al., Highly Regio-, Diastereo-, and Enantioselective C-H Insertions of Methyl Aryldiazoacetates into Cyclic N-Boc-Protected Amines. Asymmetric Synthesis of Novel C2-symmetric Amines and threo-Methylphenidate, Journal of the American Chemical Society, 1999, vol. 121, No. 27, pp. 6509-6510.
Deutsch, Howard M., et al., Synthesis and pharmacology of site specific cocaine abuse treatment agents: a new synthetic methodology for methylphenidate analogs based on the Blaise reaction, European Journal of Medicinal Chemistry, 2001, vol. 36, pp. 303-311.
Lile, Joshua A., et al., The Reinforcing Efficacy of Psychostimulants in Rhesus Monkeys: The Role of Pharmacokinetics and Pharmacodynamics, Journal of Pharmacology and Experimental Therapeutics, 2003, vol. 307, No. 1, pp. 356-366.

* cited by examiner

*Primary Examiner* — Joseph Kosack
*Assistant Examiner* — Alicia L Otton
(74) *Attorney, Agent, or Firm* — Hodgson Russ LLP

(57) ABSTRACT

Provided herein are substituted pyrrolidines that demonstrate binding at biogenic amine transporters and can be synthesized by a methodology based on a chiral dirhodium catalyst. Compositions comprising substituted pyrrolidines can be used to treat central nervous system disorders such as schizophrenia.

29 Claims, 5 Drawing Sheets

| STRUCTURE | DRUG | 5-HT Ki(nM) | SEM | DA IC50(nM) | SEM | 5-HT/DA | NE | SEM |
|---|---|---|---|---|---|---|---|---|
| (structure) | HDMP77 (ent DC-17) | >10000 | | 2080 | | | 814 | |
| (structure) | HDMP78 | 568 | | 1160 | | 0.4896552 | 1520 | |
| (structure) | HDMP79 (DC-17) | 192 | | 1290 | | 0.1488372 | 1790 | |
| (structure) | HDMP80 | 259 | 10 | 1290 | | 0.2007752 | 4850 | |
| (structure) | HDMP81 | >10000 | | 990 | 120 | | 945 | 59 |
| (structure) | HDMP82 | >10000 | | 2590 | 118 | | 2720 | 470 |
| (structure) | HDMP83 | >10000 | | 5230 | 310 | | 370 | 54 |
| (structure) | HDMP84 (DC-16) | >10000 | | 2420 | 35 | | 5980 | 1360 |
| (structure) | HDMP85 | 5600 | | 292 | 21 | | 1960 | 330 |
| (structure) | HDMP86 | >10000 | | 2883 | 681 | | 2827 | 645 |

Figure 3

| STRUCTURE | DRUG | 5-HT Ki(nM) | SEM | DA IC50(nM) | SEM | NE | SEM |
|---|---|---|---|---|---|---|---|
| (structure) | HDMP87 | >10000 | | 2156 | 100 | 1420 | 108 |
| (structure) | HDMP88 | 2300 | 620 | 277 | 34 | >10000 | |
| (structure) | HDMP89 | >10000 | | 2550 | 723 | >10000 | |
| (structure) | HDMP94 | >10,000 | | >10,000 | | 4110 | 599 |
| (structure) | HDMP95 | 838 | 135 | 2870 | 258 | 428 | 61 |
| (structure) | HDMP96 | 4570 | 830 | 3670 | 750 | 190 | 19 |
| (structure) | HDMP97 | >10,000 | | >10,000 | | 769 | 139 |

Figure 3 (continued)

| STRUCTURE | DRUG | 5-HT Ki(nM) | SEM | DA IC50(nM) | SEM | NE | SEM |
|---|---|---|---|---|---|---|---|
| Br-phenyl pyrrolidine structure, MeO₂C, OH, HCl | HDMP56 | >10000 | | >10000 | | 3943 | 323.0 |
| Naphthyl pyrrolidine structure, MeO₂C, OH, HCl | HDMP57 | >10000 | 1.166 | >10000 | | 682.4 | 128.9 |
| Cl-phenyl pyrrolidine structure, MeO₂C, OH, HCl | HDMP58 | >10000 | 6.144 | >10000 | | >10000 | |
| Cl,Cl-phenyl pyrrolidine structure, MeO₂C, OH, HCl | HDMP83 | >10000 | | 5230 | 310 | 370 | 54 |

Figure 4

SUBSTITUTED PYRROLIDINE COMPOUNDS WITH CENTRAL NERVOUS SYSTEM ACTIVITY

CROSS REFERENCE TO RELATED APPLICATIONS

This application claims priority to U.S. Provisional Application No. 60/945,746, filed on Jun. 22, 2007, the disclosure of which is incorporated herein by reference.

FIELD OF THE INVENTION

This invention relates to substituted pyrrolidine compounds having central nervous system activity.

BACKGROUND OF THE INVENTION

Central nervous system (CNS) disorders are economically and socially devastating. For example, schizophrenia is one of the leading causes of disability worldwide with a lifetime prevalence of 0.6 to 1.3% of the population characterized by high morbidity and mortality. Less than 15% of people with this disability are competitively employed, while about 20% live independently.

Schizophrenia is generally characterized by positive symptoms (such as delusions, hallucinations, and disorganized behavior), negative symptoms (such as anergia), affective symptoms (such as dysphoria, hopelessness, anxiety, hostility, aggression) and/or cognitive deficits.

Typical treatments for such disorders include drugs that affect the monoamine receptor systems. For example, the primary effect of first generation antipsychotics is dopamine (D2 receptor) blockade. While these are effective in treating the positive symptoms of schizophrenia, they exert only modest effects on negative symptoms and cognitive deficits.

Thus, despite the availability of some drugs for treating CNS disorders such as schizophrenia, there is an unmet need for improved methods and compounds for treating central nervous system disorders.

SUMMARY OF THE INVENTION

The present invention provides compositions comprising substituted pyrrolidines and methods of using same for central nervous system disorders. The compounds of the present invention have the general structure of 1. In one embodiment the Z group is a 2-naphthyl group and the compound has the general structure of 2. In another embodiment the Z group is a disubstituted phenyl group such as a 3,4-disubstituted phenyl group.

Examples of stereochemical isomers of the substituted pyrrolidines are structures 6-9. In one embodiment, the compound has the structure of DC-16 and its enantiomer. In another embodiment, the compound has the structure of DC17 and its enantiomer. In various embodiments, the compound has the structure of 12-14 and enantiomers of these compounds.

The compounds of the present invention can be used to treat or alleviate the symptoms/causes of central nervous system disorders.

BRIEF DESCRIPTION OF THE DRAWINGS

FIG. 3. Table of receptor inhibition data.
FIG. 4. Table of receptor inhibition data.

DESCRIPTION OF THE INVENTION

Figure 1:
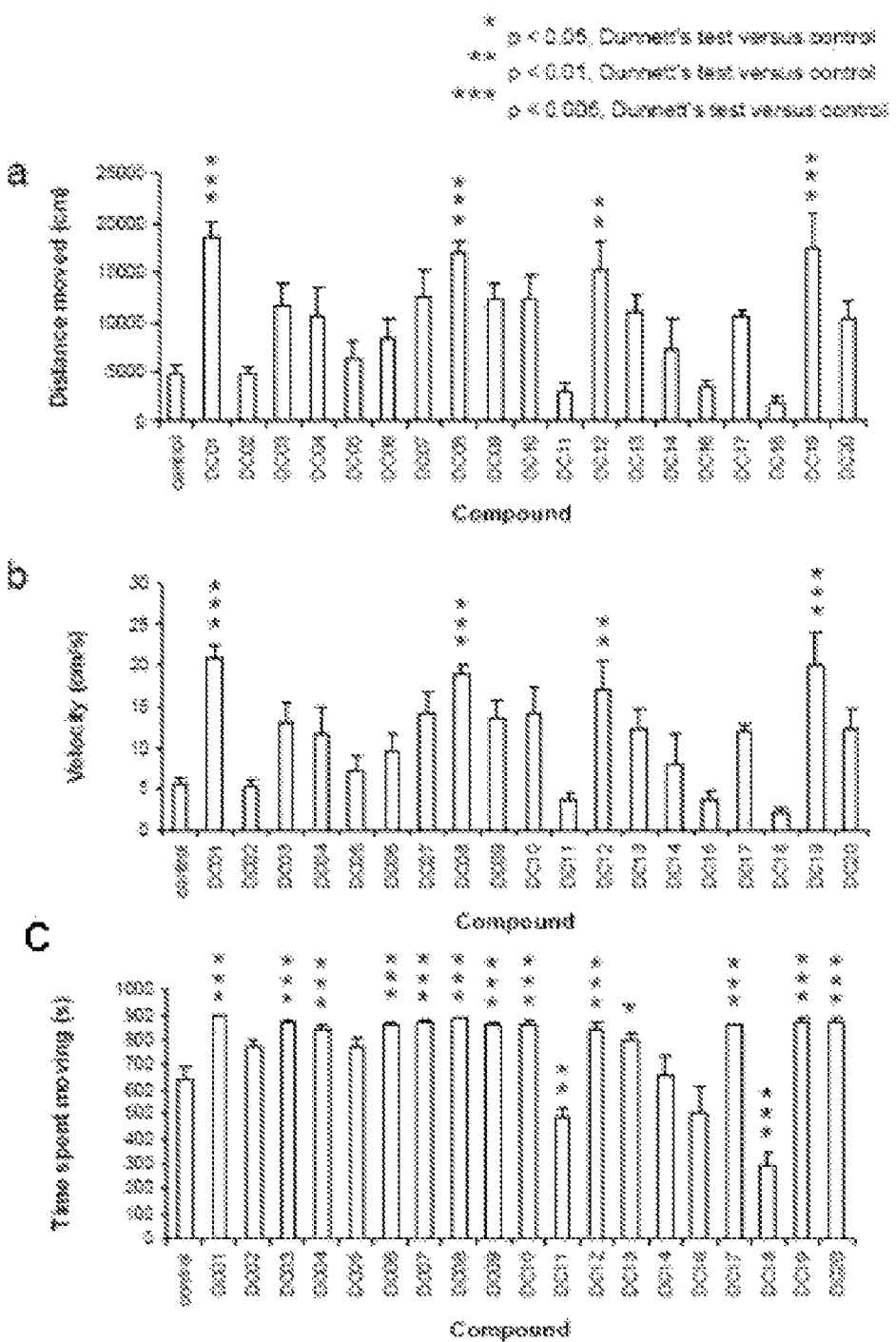
FIG. 1
(a) Graphical representation of movement data from ckr mouse screening test.
(b) Graphical representation of velocity data from ckr mouse screening test.
(c) Graphical representation of temporal data from ckr mouse screening test.

The present invention provides compositions of substituted pyrrolidine compounds that can function as monoamine transporter inhibitors, and act as selective serotonin transporter (SERT) inhibitors. These compounds can be used for alleviating the symptoms of CNS disorders.

The compounds of the present invention have the following general structure (structure (1)):

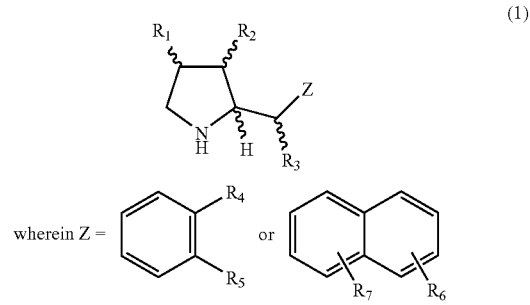

The substituents on the pyrrolidine ring, $R_1$ and $R_2$ can be H, hydroxy or alkoxy (ORx), carboxylic acid or carboxylate (C(O)ORx), or amido (C(O)N(Rx)Rx (the amido group can be unsubstituted (both Rx groups are H; $C(O)NH_2$) or substituted (one or both Rx groups are not H; C(O)NHRx or C(O)N(Rx)Rx)). Rx can be a hydrogen, alkyl (such as —$CH_3$) or alkenyl group (a group with a carbon-carbon double bond) comprising 8 carbons or less, aryl group (a cyclic aromatic hydrocarbon that can be substituted or unsubstituted), or amino group (including substituted or unsubstituted amines). Regarding the $R_1$ and $R_2$ substituents, if $R_1$ is ORx, C(O)ORx or C(O)N(Rx)Rx, then $R_2$ is H and the compound is a 2,4-substituted pyrrolidine. If $R_2$ is ORx, C(O)ORx or C(O)N(Rx)Rx, then R1 is H and the compound is a 2,3-substituted pyrrolidine. $R_3$ can be C(O)ORy or $CH_2ORy$, and Ry is a hydrogen, alkyl or alkenyl group comprising 8 carbons or less, aryl group, or amino group.

$R_4$ can be an alkyl, aryl, alkenyl, alkoxy, halo (fluoro, chloro, bromo, or iodo), nitro (—$NO_2$), cyano (—CN), keto (—C(O)R, where R is an alkyl chain comprising 8 carbons or less), amino, or carboxylate group. $R_5$ can be an alkyl, aryl, alkenyl, alkoxy, halo, nitro, cyano, keto, amino, carboxylate group. $R_6$ can be alkyl, aryl, alkenyl, alkoxy, halo, nitro, cyano, keto, amino, carboxylate. $R_7$ can be alkyl, aryl, alkenyl, alkoxy, halo, nitro, cyano, keto, amino, carboxylate.

In one embodiment the Z group of the compound is a 2-naphthyl group and the compound has general structure (2) or its enantiomer (3).

(2)

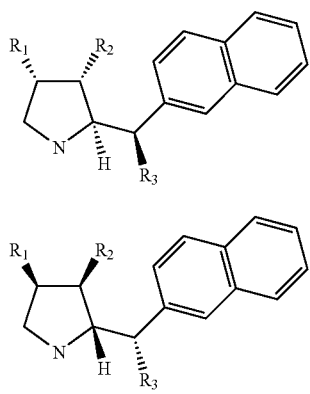

(3)

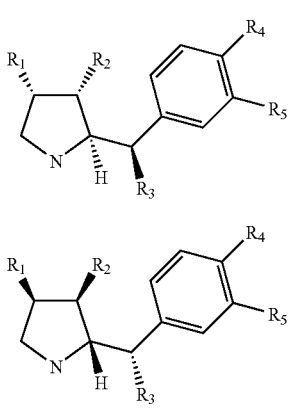

In one embodiment the Z group of the compound is a 3,4-disubstituted phenyl group and the compound has the general structure of 4 or its enantiomer 5.

(4)

(5)

In another embodiment the Z group of the compound is a disubstituted phenyl group (such as 2,3-, or 2,4-disubstituted).

The present invention includes all stereoisomers (including enantiomers and diastereomers) that can be formed from the various substitutions and orientations of structure 1. In one embodiment the compound has diastereomeric structure 6 or its enantiomer (structure 7), which can be prepared by the general synthetic methodology described in Example 1.

(6)

(7)

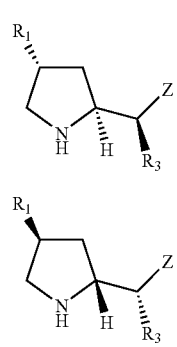

In another embodiment the compound has diastereomeric structure 8 or its enantiomer (structure 9), which can be prepared by the general synthetic methodology described in Example 1.

(8)

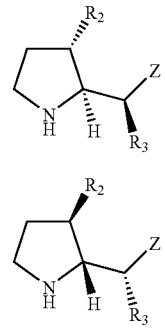

(9)

Examples of compounds of the present invention include, but are not limited to, the following structures and their enantiomers:

(10)

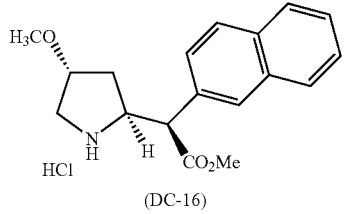

(DC-16)

(11)

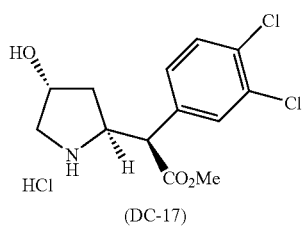

(DC-17)

(12)

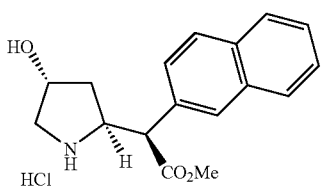

(13)

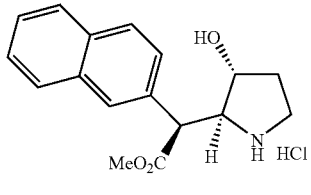

(14)

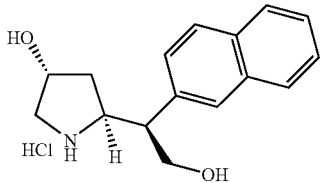

As an illustration, compounds DC16 and DC-17 were observed to show favorable biological activity based on receptor binding data and ckr mouse testing results.

The compositions can comprise enantiomers or racemic mixtures of these compounds as well. The compounds above can have other stereochemical configurations, where one or two of the stereocenters have been inverted. This includes the threo-diastereomeric structure in which the stereocenter in the side chain group has been inverted. It also includes the diastereomeric series where the stereocenter in the ring ($R_1$ and/or $R_2$) have been inverted. The compositions can comprise a diastereomeric mixture of these stereoisomers as well as their enantiomers.

These compounds may be administered orally, parenterally, intramuscularly, intravenously, mucosally or by other route. Other ingredients may be added to the compounds as part of the pharmaceutical composition depending on the dosage form, particular needs of the patient, and method of manufacture, among other things. Examples include, but are not limited to, binders, lubricants, fillers, flavorings, preservatives, colorings, diluents, etc. The selection of particular substances and their compatibilities with the compositions of the present invention can be readily ascertained by those of ordinary skill in the art. Details are also provided in U.S. Pat. No. 5,763,455, which is incorporated herein by reference. In one embodiment, the route of administration is oral. The dosage regimen of these compounds is well within the purview of those skilled in the art. By way of example, the dose levels may be from 4 micrograms per kilogram of body weight up to 50 milligrams/Kg of body weight. By way of another example, the dose may be from 20 micrograms/Kg up to 15 mg/Kg.

The chakragati (ckr) mouse model was used to demonstrate the in vivo efficacy of the presently claimed compositions in reducing symptoms of neuropsychiatric disorders. (See Example 4) The efficacy of the compositions is demonstrated using a mouse model described in U.S. Pat. No. 5,723,719, the description of which is incorporated herein by reference.

The ckr mouse model is a transgenic mouse which exhibits motor activity and social behaviors characteristic of schizophrenia. The ckr mouse was serendipitously created as a result of a transgenic insertional mutation. The apparent loss-of function of endogenous genes and associated genetic rearrangements resulted in a transgenic mouse that in the homozygous condition, exhibited an abnormal circling phenotype. The increased motor activity in these mice is similar to that observed in wild-type mice treated with NMDA (N-methyl-D-aspartic acid) receptor antagonists, which produce behaviors resembling the positive symptoms of schizophrenia. The ckr mouse also appears to show reduced social interactions resembling the social withdrawal that is part of the constellation of negative symptoms of schizophrenia. The mouse also presents lateral ventricular enlargement, which may mirror neuropathological observations in schizophrenia. Atypical antipsychotics clozapine and olanzapine have been shown to reduce the characteristic circling behavior of the mice. These data collectively suggest that the ckr mouse may model certain aspects of the pathology of schizophrenia.

The model has been further validated by testing risperidone, haloperidol and pimozide in the ckr mouse. The behavioral output was assayed by measuring the rate of hyperactivity and circling after administration. The results demonstrated a dose-dependent attenuation of hyperactivity in ckr mice for risperidone, clozapine, haloperidol and pimozide in concentrations relevant to human clinical use. Based on the foregoing, the ckr mouse model is considered to be valid for evaluation of compounds for use in reducing the symptoms of neuropsychiatric disorders in mammals, including humans.

Dysfunctions in information processing and attentional processes are important aspects of the deficits in schizophrenia. Deficits in sensorimotor gating and processing of the relevance of stimuli are central to many aspects of the symptomatology of schizophrenia. It is therefore important that animal models of schizophrenia also model these deficits in sensory information processing. Pre-pulse inhibition (PPI) is a sensorimotor gating phenomenon, which results in reduced responses to a strong stimulus when it is preceded by a pre-pulse exposure to the stimulus at a lower intensity that does not elicit the response. PPI is commonly measured as the reduction of the startle response to a loud white-noise pulse by pre-exposure to a weaker white-noise pre-pulse. PPI is deficient in patients with schizophrenia. This deficiency in PPI is generally considered to reflect disturbances in sensorimotor gating. In animal models, the PPI test is considered to have good face, predictive, and construct validity for sensorimotor gating deficits in schizophrenia and PPI deficits have been an important criterion in the assessment of animal models of schizophrenia, including both hypoglutamatergic and hyperdopaminergic models.

To obtain the ckr mouse model data presented in Example 4, a variety of related compounds, including compounds of the present invention, were used to investigate a standard measure of sensorimotor gating of the startle reflex. Sensorimotor gating of the startle reflex was assessed via measures of PPI, which is the reduction in startle magnitude when the startling stimulus is preceded immediately by a weak pre-pulse. This measurement is valuable because the relative loss of PPI has been established in inherited neurodevelopmental disorders, such as schizophrenia in humans, as well as in rats after treatment with certain classes of drugs, including serotonin (5-HT) agonists.

The data of the in vitro binding affinities at monoamine transporters (FIGS. 3 and 4) and the in vivo ckr mouse studies (FIGS. 1 and 2) demonstrate that these highly substituted pyrrolidines have biological activity as CNS agents and in particular for the treatment of depression and schizophrenia.

The following examples are provided for illustrative purposes only and are not intended to be limiting in any manner.

EXAMPLE 1

Synthesis of Substituted Pyrrolidine Compounds

This example describes the synthesis of compounds of the present invention. In one embodiment, a substituted pyrrolidine ((R)-methyl 2-((2S,4R)-4-hydroxypyrrolidin-2-yl)-2-(naphthalen-2-yl)acetate hydrochloride) (HDMP-80) was synthesized using a C—H activation step. This reaction preferentially forms the eyrthro product with high diastereo- and enantioselectivity. The reaction is catalyzed by a chiral catalyst, $Rh_2(S\text{-}DOSP)_4$, that controls which position of the pyrrolidine ring is functionalized (C2 or C5).

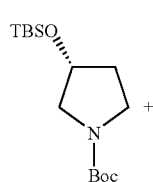

-continued

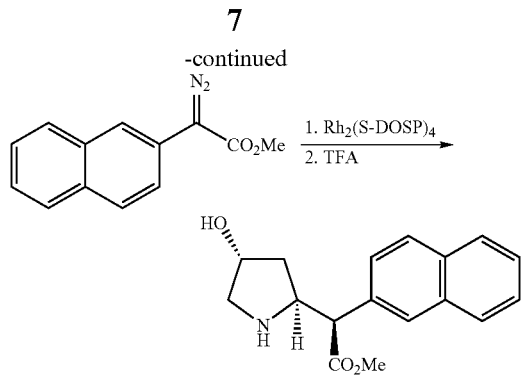

Generally, synthesis of the substituted pyrrolidines of the present invention was achieved using the reaction scheme shown above. For example, a variety of methyl aryldiazoacetates can be reacted with 3-substituted, N-Boc-protected pyrrolidines (in the case of hydroxy-substituted pyrrolidines) to generate 2,4-disubstituted and 2,3-disubstituted pyrrolidine derivatives. The diastereoselectivity of the products is, generally, greater than 95 percent when starting with enantiomerically pure or substantially pure substituted pyrrolidines. Hydroxy-substituted pyrrolidines are protected as silyl ester derivatives, which can be treated with trifluoroacetic acid to generate the free hydroxyl substituent on the pyrrolidine ring. Methoxy-substituted pyrrolidines are also suitable substrates. The functionality obtained in these transformations is very difficult to achieve using conventional chemistry. Thus, the process allows ready access for biological evaluation of substantially pure stereoisomers of highly substituted pyrrolidines

EXAMPLE 2

Synthesis of (R)-methyl 2-((2S,4R)-4-methoxypyrrolidin-2-yl)-2-(naphthalen-2-yl)acetate hydrochloride (DC-16) and (S)-methyl 2-((2R,3R)-3-methoxypyrrolidin-2-yl)-2-(naphthalen-2-yl)acetate hydrochloride (HDMP85)

A stirred solution of (R)-3-(methoxy)-N-(tert-butoxycarbonyl)pyrrolidine (0.63 g) and dirhodium(II) tetrakis[(S)—N-[p-(dodecylphenyl)sulfonyl]prolinate] {Rh$_2$(S-DOSP)$_4$} (113 mg) in 2,2-dimethylbutane (50 mL) was stirred under reflux. Diazo-(2-naphthylacetic acid methyl ester) (1.41 g) in a 1:4 mixture of trifluorotoluene: 2,2-diethylbutane was added via syringe pump over a 3 hour period. The mixture was stirred under reflux for an additional 2 hours and then stirred at room temperature overnight. The mixture was then concentrated, diluted with dichloromethane (100 mL) and charged with trifluoroacetic acid (1.97 mL, 26.6 mmol). After 16 hours, the solution was concentrated, the residue dissolved in Et$_2$O (100 mL), and extracted with 10% HCl (3×100 mL). The aqueous layers were basified with solid NaHCO$_3$ (solid) and 1M NaOH to pH=8–9. The aqueous phase was then back extracted ethyl acetate (3×50 mL) and the organic phases were washed with brine (25 mL), dried with Na$_2$SO$_4$, and filtered. The extraction was reduced and purified by chromatography to afford a 1:2.6 mixture of (R)-methyl 2-((2S,4R)-4-methoxypyrrolidin-2-yl)-2-(naphthalen-2-yl)acetate hydrochloride (DC-16) and (S)-methyl 2-((2R,3R)-3-methoxypyrrolidin-2-yl)-2-(naphthalen-2-yl)acetate hydrochloride: 391 mg (549 mg, 59% yield). The two regioisomers are separated by silica gel chromatography. (R)-methyl 2-((2S,4R)-4-methoxypyrrolidin-2-yl)-2-(naphthalen-2-yl)acetate. (DC-16): [α]$^D_{23}$=+64.2 (c=1.2, CHCl$_3$); $^1$H NMR (500 MHz, CDCl$_3$) δ 7.82-7.79 (m, 4H), 7.52-7.43 (d, J=7 Hz, 3H), 4.04-3.98 (m, 2H), 3.92 (s, 1H), 3.30 (s, 3H), 3.12-3.07 (m, 1H), 2.87-2.84 (m, 1H), 2.20-2.15 (m, 1H), 1.69-1.62 (m, 2H). $^{13}$C NMR (75 MHz, CDCl$_3$) δ 172.9 (C), 134.8 (C), 133.3 (C), 132.7 (C), 128.3 (CH), 127.8 (CH), 127.5 (CH), 126.1 (CH), 125.9 (CH), 81.2 (CH), 59.5 (CH), 57.8 (CH$_3$), 56.3 (CH$_2$), 51.9 (CH), 51.8 (CH$_2$), 36.5 (CH$_3$). IR (neat): 1732 cm$^{-1}$; HRMS (ESI) m/z Calc'd for [C$_{18}$H$_{21}$NO$_3$]+(M+23): 299.1521. Found 322.1412. (S)-methyl 2-((2R,3R)-3-methoxypyrrolidin-2-yl)-2-(naphthalen-2-yl)acetate: [α]$^D_{23}$=−174.2 (c=1.0, CHCl$_3$); $^1$H NMR (500 MHz, CDCl$_3$) δ 7.83-7.80 (m, 4H), 7.57-7.55 (d, 1H), 7.48-7.43 (m, 2H), 3.84-3.83 (d, 1H), 3.72-3.64 (m, 4H), 3.34 (s, 3H), 3.03-2.88 (m, 2H), 1.99-1.92 (m, 1H), 1.87-1.82 (m, 1H), 1.65 (bs, 1H). $^{13}$C NMR (75 MHz, CDCl$_3$) δ 172.9 (C), 134.1 (C), 133.3 (C), 132.8 (C), 128.3 (CH), 127.9 (CH), 127.6 (CH), 126.4 (CH), 125.9 (CH), 84.4 (CH), 65.7 (CH), 56.8 (CH$_3$), 55.4 (CH$_2$), 51.9 (CH), 44.2 (CH$_2$), 30.9 (CH$_3$). IR (neat): 1732 cm$^{-1}$; HRMS (ESI) m/z Calc'd for [C$_{18}$H$_{21}$NO$_3$]$^+$ (M+23): 299.1521. Found 322.1412.

The neutral bases were converted to the hydrochloride salts by dissolving the base in dry ether followed by addition of ethereal HCl and isolation of the salt by filtration. The enantiomeric series of compounds was prepared by starting with the enantiomer of the catalyst and the substrate described above.

Synthesis of (R)-methyl 2-(3,4-dichlorophenyl)-2-((2S,4R)-4-hydroxypyrrolidin-2-yl)acetate hydrochloride (DC-17).

A stirred solution of (R)-3-(tert-butyldimethylsilyloxy)-N-(tert-butoxycarbonyl)pyrrolidine (1.00 g, 3.32 mmol) and dirhodium(II) tetrakis[(S)—N-[p-(dodecylphenyl)sulfonyl]prolinate] {Rh$_2$(R-DOSP)$_4$} (125 mg, 0.07 mmol) in 2,2-dimethylbutane was stirred under reflux. Diazo-(3,4-dichlorophenyl)acetic acid methyl ester (1.63 g, 6.64 mmol) in a 1:4 mixture of trifluorotoluene: 2,2-diethylbutane was added via syringe pump over a 3 hour period. The mixture was stirred under reflux for an additional 2 hours and then stirred at room temperature overnight. The mixture was then concentrated, diluted with dichloromethane (100 mL) and charged with trifluoroacetic acid (1.97 mL, 26.6 mmol). After 16 hours, the solution was concentrated, the residue dissolved in Et$_2$O (100 mL), and extracted with 10% HCl (3×100 mL). The aqueous layers were basified with solid NaHCO$_3$ (solid) and 1M NaOH to pH=8–9. The aqueous phase was then back extracted ethyl acetate (3×50 mL) and the organic phases were washed with brine (25 mL), dried with Na$_2$SO$_4$, and filtered. The extraction was reduced and purified by chromatography to afford the titled compound as a clear oil: 391 mg (35% yield). $^1$H NMR (500 MHz, CDCl$_3$) δ 7.50 (s, 1H), 7.41-7.39 (d, J=8 Hz, 1H), 7.24-7.22 (m, 1H), 4.41 (m, 1H), 3.99 (m, 1H), 3.67 (s, 1H), 3.42 (d, J=9 Hz, 1H), 3.04 (dd, J=4.5, 7.5 Hz, 1H), 2.83 (m, 1H), 2.00 (m, 4H), 1.66 (m, 1H). $^{13}$C NMR (75 MHz, CDCl$_3$) δ 172.3 (C), 137.4 (C), 132.7 (C), 131.8 (C), 130.6 (CH), 130.5 (CH), 128.1 (CH), 72.3 (CH), 59.3 (CH$_2$), 56.6 (CH), 54.8 (CH), 52.2 (CH$_3$), 40.2 (CH$_2$); IR (neat): 1753 cm$^{-1}$; HRMS (ESI) m/z Calc'd for [C$_{13}$H$_{15}$Cl$_2$NO$_3$]$^+$ (M$^+$): 303.0429. Found: 303.0437.

The neutral base was converted to the hydrochloride salt by dissolving the base in dry ether followed by addition of ethereal HCl and isolation of the salt by filtration. The enantiomer was prepared by starting with the enantiomers of the catalyst and the substrate described above.

Synthesis of (R)-methyl 2-((2S,4R)-4-hydroxypyrrolidin-2-yl)-2-(naphthalen-2-yl)acetate (HDMP 80).

A stirred solution of (R)-(tert-butyldimethylsilyloxy)-N-(tert-butoxycarbonyl)pyrrolidine (0.837 g) and dirhodium(II) tetrakis[(S)—N-[p-(dodecylphenyl)sulfonyl]prolinate] {Rh$_2$(S-DOSP)$_4$} (104 mg) in 2,2-dimethylbutane (50 mL) was stirred under reflux. Diazo-(2-naphthyl)acetic acid methyl ester (1.63 g, 6.64 mmol) in a 1:10 mixture of trifluorotolune: 2,2-diethylbutane was added via syringe pump over a 3 hour period. The mixture was stirred under reflux for an additional 2 hours and then stirred at room temperature overnight. The mixture was then concentrated, diluted with dichloromethane (100 mL) and charged with trifluoroacetic acid (1.97 mL). After 16 hours, the solution was concentrated, the residue dissolved in $Et_2O$ (100 mL), and extracted with 10% HCl (3×100 mL). The aqueous layers were basified with solid $NaHCO_3$ (solid) and 1M NaOH to pH=8–9. The aqueous phase was then back extracted ethyl acetate (3×50 mL) and the organic phases were washed with brine (25 mL), dried with $Na_2SO_4$, and filtered. The extraction was reduced and purified by chromatography to afford the titled compound as a clear oil: (672 mg, 64% yield). $[\alpha]^D_{23}$=+74.20 (c=1.0, $CHCl_3$); $^1H$ NMR (500 MHz, $CDCl_3$) δ 7.83-7.80 (m, 4H), 7.53-7.51 (m, 1H), 7.47-7.45 (m, 2H), 4.44 (m, 1H), 4.15-4.10 (m, 1H), 3.67 (m, 4H), 3.14-3.10 (dd, J=6, 5 Hz, 1H), 2.82-2.79 (m, 1H), 2.09-2.04 (m, 1H), 1.81-1.75 (m, 3H). $^{13}C$ NMR (75 MHz, $CDCl_3$) δ 173.0 (C), 134.7 (C), 133.4 (C), 132.8 (C), 128.5 (CH), 127.9 (CH), 127.7 (CH), 127.6 (CH), 126.2 (CH), 126.2 (CH), 125.9 (CH), 72.4 (CH), 59.3 ($CH_2$), 57.6 (CH), 54.8 ($CH_3$), 51.9 (CH), 40.4 ($CH_2$); IR (neat): 1720 $cm^{-1}$; HRMS (ESI) m/z Calc'd for $[C_{17}H_{19}NO_3]$+ (M+): 285.13649. Found 286.1370.

The neutral base was converted to the hydrochloride salt by dissolving the base in dry ether followed by addition of ethereal HCl and isolation of the salt by filtration. The enantiomer was prepared by starting with the enantiomers of the catalyst and the substrate described above.

Synthesis of (3R,5S)-5-((R)-2-(hydroxy-1-(naphthalen-2-yl)ethyl)pyrrolidin-3-ol hydrochloride (HDMP 86).

A one neck 25 mL flask was charged with ((R)-methyl 2-((2S,4R)-4-hydroxypyrrolidin-2-yl)-2-(naphthalen-2-yl)acetate (89 mg, 0.27 mmol) in THF (4 mL) and stirred at −78° C. for 30 min. Lithium aluminum hydride (0.1 mL) (3M in THF) was added drop-wise. It was allowed to stir and warm an additional 16 hours. The mixture was quenched drop-wise with 4M NaOH (1 mL) and $H_2O$ (1 mL). Celite was added and the mixture was filtered. The supernatant liquid was concentrated and purified via flash column chromatography (1:1:3; MeOH: $Et_3N$: EtOAc; $SiO_2$,) to afford the titled compound: 56 mg, 81% yield). $[\alpha]^D_{23}$=−87.1 (c=1.0, $CHCl_3$); $^1H$ NMR (500 MHz, $CDCl_3$) δ 7.93-7.65 (m, 4H), 7.41-7.28 (m, 3H), 3.82 (m, 2H), 3.32 (m, 1H) 3.12 (m, 1H), 3.08 (m, 1H), 2.90 (m, 2H), 1.70 (m, 2H), 1.65 (bs, 2H). $^{13}C$ NMR (75 MHz, $CDCl_3$) δ 137.4 (C), 135.0 (C), 134.5 (C), 129.9 (CH), 128.7 (CH), 128.6 (CH), 127.5 (CH), 127.2 (CH), 127.2 (CH), 70.7 (CH), 64.9 ($CH_2$), 62.6 ($CH_2$), 54.2 (CH), 39.6 ($CH_2$); HRMS (ESI) m/z Calc'd for $[C_{16}H_{19}NO_2]$ (M+1): 257.14158. Found 258.14958.

The neutral base was converted to the hydrochloride salt by dissolving the base in dry ether followed by addition of ethereal HCl and isolation of the salt by filtration. The enantiomer was prepared by starting with the enantiomers of the catalyst and the substrate described above.

EXAMPLE 3

Determination of Interaction of Substituted Pyrrolidine Compounds with Receptors Relating to CNS Disorders Binding Studies.

Binding of substituted pyrrolidine compounds at biogenic amine transporters was determined using striatum and frontal cortex dissected from frozen Sprague-Dawley rat brains (Pel-Freez, Rogers, Ark.). Affinities of the compounds at dopamine (DA) transport sites were determined by displacement of $[^{125}I]$ 3 beta-(4-iodophenyl)tropan-2 beta-carboxylic acid methyl ester (RTI-55) binding in membranes from rat striatum, using 0.5 mg (original wet weight) of membranes and 10 pM $[^{125}I]$RTI-55. Non-specific binding was determined in the presence of 1 μM 2β-propanoyl-3β-(2-naphthyl) tropane (WF-23). Affinities of the compounds at 5-HT transport sites were determined by displacement of $[^3H]$paroxetine binding in membranes from rat frontal cortex, using 50 mg (original wet weight) of membranes and 0.4 nM $[^3H]$paroxetine. Non-specific binding was determined in the presence of 10 μM fluoxetine. Binding of the compounds at norepinephrine (NE) transport sites was determined by displacement of $[^3H]$nisoxetine binding in membranes from rat forebrain, using 0.7 nM $[^3H]$nisoxetine. Non-specific binding was determined in the presence of 1 μM desipramine.

Potencies in FIGS. 3 and 4 were calculated from displacement curves using 7-10 concentrations of unlabeled compounds, as analyzed by non-linear curve fitting. Because the binding of substituted pyrrolidines at dopamine transporters is generally regarded as multiphasic, potencies in inhibiting $[^{125}I]$RTI-55 binding are reported as $IC_{50}$ values. For $[^3H]$paroxetine and $[^3H]$nisoxetine binding assays, Ki values were calculated using the Cheng-Prusoff equation. All data are mean values ±SEM (standard error measurement) of at least three separate experiments, each of which was conducted in triplicate.

Biological Activity.

The binding affinities to dopamine (DA), serotonin (5-HT), and norepinephrine (NE) transporters for the series of compounds listed in FIGS. 4 and 5 were determined by methods described above.

The compounds of the present invention displayed biological activity, many having desirable binding affinities to dopamine and norepinephrine transporters. Compounds binding to more than one monoamine transporter have been shown to be effective as antidepressants and so, the substituted pyrrolidine derivatives of the present invention are expected to have similar activity. A preferred compound is HDMP-80 which shows high binding affinity for the serotonin transporter.

EXAMPLE 4

Screening Candidate Compounds Using ckr Mouse Model

To test the effect of compounds, including compounds of the present invention, on CNS function, chakragati (ckr) mice were used as a model. The DC series compounds were tested on motor activity and PPI in ckr mice.

Preparation of Drug Solutions.

Stock solutions of the drugs (DC1 to DC20) were dissolved in DMSO, and then diluted to 10 mg/10 mL with distilled water such that the final concentration of DMSO was 0.5%. Each animal received 10 mg/kg of the test drug in a volume of 0.1 mL per 10 g. Some compounds (DC9, DC11, DC 12, DC13 and DC16) proved difficult to dissolve in DMSO alone. These compounds were sonicated for 30 minutes in DMSO, acidified to pH 4 to 5 by drop-wise addition of 1M HCl, and then suspended in 20% cyclodextrin solution.

Screening of Candidate Compounds Based on Motor Activity.

Twenty ckr mice (male and female, 3 months old) were randomly assigned to receive test drugs or 0.5% DMSO vehicle. Each drug was tested in 5 mice. Each mouse received up to 5 randomly assigned drugs in random order. Each treatment was separated by a minimum washout period of 3 days. On the day of testing, mice were brought into the behavioral test room and allowed to acclimatize for at least 1 hour. They then received intraperitoneal injections of the 0.1 mL/10 g (10 mg/kg) of the test drug solutions or vehicle.

They were returned to their cage and 20 minutes later they were placed in a 190 mm diameter, 300 mm deep circular recording chamber. Four mice were tested simultaneous in 4 separate chambers. Between each testing session the chambers were wiped down with 70% ethanol and allowed to dry for at least 10 minutes The mice were monitored with an overhead video camera for 15 min. Their behavior was videotaped and simultaneously digitized and tracked (Ethovision Version 2, Noldus). The total distance moved, the velocity of movement, and the time spent moving were calculated.
Screening of Candidate Compounds Based on Pre-Pulse Inhibition of Acoustic Startle.

Selected compounds with significant effects on movement were tested for effects on PPI. These compounds were DC01, DC08, DC11, DC 12, DC 16, DC18, and DC19. Eighteen ckr mice (male and female, 3 months old) were randomly assigned to receive test drugs or vehicle. Each drug or vehicle was tested in 6 to 7 mice. Each mouse received up to 4 randomly assigned drugs in random order. Each treatment was separated by a minimum washout period of 3 days.
Apparatus Startle reactivity was measured using a startle chamber (SR-LAB, San Diego Instruments, San Diego, Calif.). The chamber consisted of a clear plexi-glass cylinder resting on a platform inside a ventilated, sound-attenuating chamber. A high frequency loudspeaker inside the chamber produced both a continuous background noise of 65 dB as well as the various acoustic stimuli. Vibrations of the plexi-glass cylinder, caused by the whole body startle response of the animals, were transduced into analog signals (0 to 5,000 mV range) by a piezoelectric unit attached to the platform. These signals were then digitized for analysis.
Procedure There were 8 mice in each group. The mice were acclimatized for 60 minutes in the behavioral test room prior to measurement of PPI. They were then placed in the plexiglass cylinder and exposed to 65 dB background white-noise. After 5 minutes, the mice were exposed to a series of 5 different types of trials involving exposure to pulses of white-noise: (1) pulse-alone trials, during which a 120 dB stimulus was presented for 40 milliseconds (ms); (2)+3 dB pre-pulse trials, during which a 20 ms, 68 dB (+3 dB above 65 dB background) pre-pulse preceded the 120 dB pulse by the pre-pulse to pulse interval; (3)+6 dB pre-pulse trials, during which a 20 ms, 71 dB (+6 dB above 65 dB background) pre-pulse preceded the 120 dB pulse by the pre-pulse to pulse interval; (4)+12 dB pre-pulse trials, during which a 20 ms, 77 dB (+12 dB above 65 dB background) pre-pulse preceded the 120 dB pulse by the pre-pulse to pulse interval; and (5) no pulse trials. For the measurement of differences in PPI between the wild-type, heterozygous and ckr mice, the pre-pulse to pulse interval was set at 100 ms. A characteristic of pre-pulse inhibition is that the phenomenon disappears at very short pre-pulse to pulse intervals. In the ckr mice, the protocol was subsequently repeated with 25 ms, 100 ms, and 175 ms pre-pulse to pulse intervals in pseudorandom order to confirm that the effect seen was a pre-pulse inhibition. In one session, a total of 52 trials were conducted in pseudorandom order: 20 pulse alone trials, and 8 each of the other four trials. These were preceded by 4 pulse alone trials, which were discarded. The average inter-trial interval was 15 seconds (9-21 second range). The startle response was recorded as the average movement detected over 65 ms following the pulse. Cases were the startle response amplitude on the pre-pulse trial exceeded 90% of the average startle response amplitude on the pulse alone trials were excluded. The startle amplitude was measured as the average startle response for the pulse-alone trials. Pre-pulse inhibition was calculated as percentage PPI, namely as $(A-B)/A \times 100$, where A was the average startle response amplitude on pulse-alone trials and B was the average startle response amplitude on pre-pulse trials. Use of this measure, in preference to absolute difference scores, minimizes the possible effects of individual differences in startle amplitude on PPI.
Results of ckr Mouse Screening Tests.
Statistical Analysis.

The data for each parameter were separately analyzed by one-way ANOVA (Analysis of Variance) and post hoc Dunnett's comparisons with the vehicle-treated control group. Tukey's HSD test was applied for post hoc comparisons between groups. $p < 0.05$ was considered statistically significant.
General Observations on Response to DC Series Drug Administration.

DC15 proved lethal at 10 mg/kg in 3 mice. Treatment with DC15 was discontinued. There was no evidence of adverse physiological effects observed with any of the other DC series drugs. Other than changes in the patterns of motor activity reported the ckr circling behavior reported here, there were no drug-induced abnormalities in behavior observed.
Motor Activity Results.
Total Distance Move The overall effect of the DC series drugs on the total distance moved was significant ($F19,75=5.839$, $p<0.0001$). DC01, DC08, DC12 and DC19 significantly increased the total distance moved (FIG. 1a). DC11, DC16 and DC18 produce a trend towards decreased total distance moved.
Velocity The overall effect of the DC series drugs on the total distance moved was significant ($F19,75=5.721$, $p<0.0001$). DC01, DC08, DC12 and DC19 significantly increased velocity (FIG. 1b). DC11, DC16 and DC18 produce a trend towards decreased velocity.
Time Spent Moving The overall effect of the DC series drugs on the total distance moved was significant ($F19,75=22.99$, $p<0.0001$). DC01, DC08, DC12 and DC19 significantly increased the total distance moved as did several other drugs in the series (FIG. 1c). DC11 and DC18 significantly decreased the time spent moving. DC16 produces a trend towards a decrease in the time spent moving.
Pre-Pulse Inhibition of Acoustic Startle Results:
Startle Amplitude The overall DC series drug effect on startle amplitude was significant ($F7,44=2.573$, $p<0.05$). However, there were no significant differences from the vehicle-treated control group (FIG. 2a). The difference was attributable to elevation of startle amplitude on treatment with DC01 above that on treatment with DC11 ($p<0.05$) and DC16 ($p<0.05$).
Pre-Pulse Inhibition For pre-pulses 3 dB above background, the effect of drug treatment was significant ($F7,28=2.718$, $p<0.05$). DC11 significantly increased PPI over the vehicle control ($p<0.05$), while DC12, DC16 and DC18 produced similar but insignificant trends (FIG. 2b). For pre-pulses 6 dB above background, the effect of the drug treatment was also significant ($F7, 29=4.087$, $p<0.005$). DC11 significantly increased PPI over the vehicle control ($p<0.05$), while only DC18 produce a similar but insignificant trend (FIG. 2c). For pre-pulses 12 dB above background, the effect of the drug treatment was again significant (F7,31=8.039, p<0.0005). DC11 and DC12 both increased PPI over the vehicle control (p<0.01 and p<0.05, respectively), while DC18 produced a similar but insignificant trend (FIG. 2 d). In summary, DC11 consistently produced significant recovery of PPI, while only DC18 produced a similar trend across all pre-pulse intensities.

Discussion of Results.

DC11 and DC18 produced decreases in motor activity in the circling ckr mice and a trend towards amelioration of the deficits in PPI seen in the ckr mouse. The present data suggest these compounds are candidate antipsychotic drugs that are active in the central nervous system after systemic administration. DC01, DC08, DC12 and DC19 increased motor activity but had little consistent effect on PPI. Increases, in motor activity are likely to relate to increases in dopaminergic function. Importantly the effect on circling in the ckr mouse suggests that these drugs are bioavailable in the central nervous system after systemic administration. That these drugs did not alter PPI or worsen the deficits in PPI in the ckr mouse suggests that they are unlikely to produce severe sensorimotor processing deficits. The profile of these drugs suggests that they are centrally active after systemic administration and increase dopaminergic function.

Figure 2:
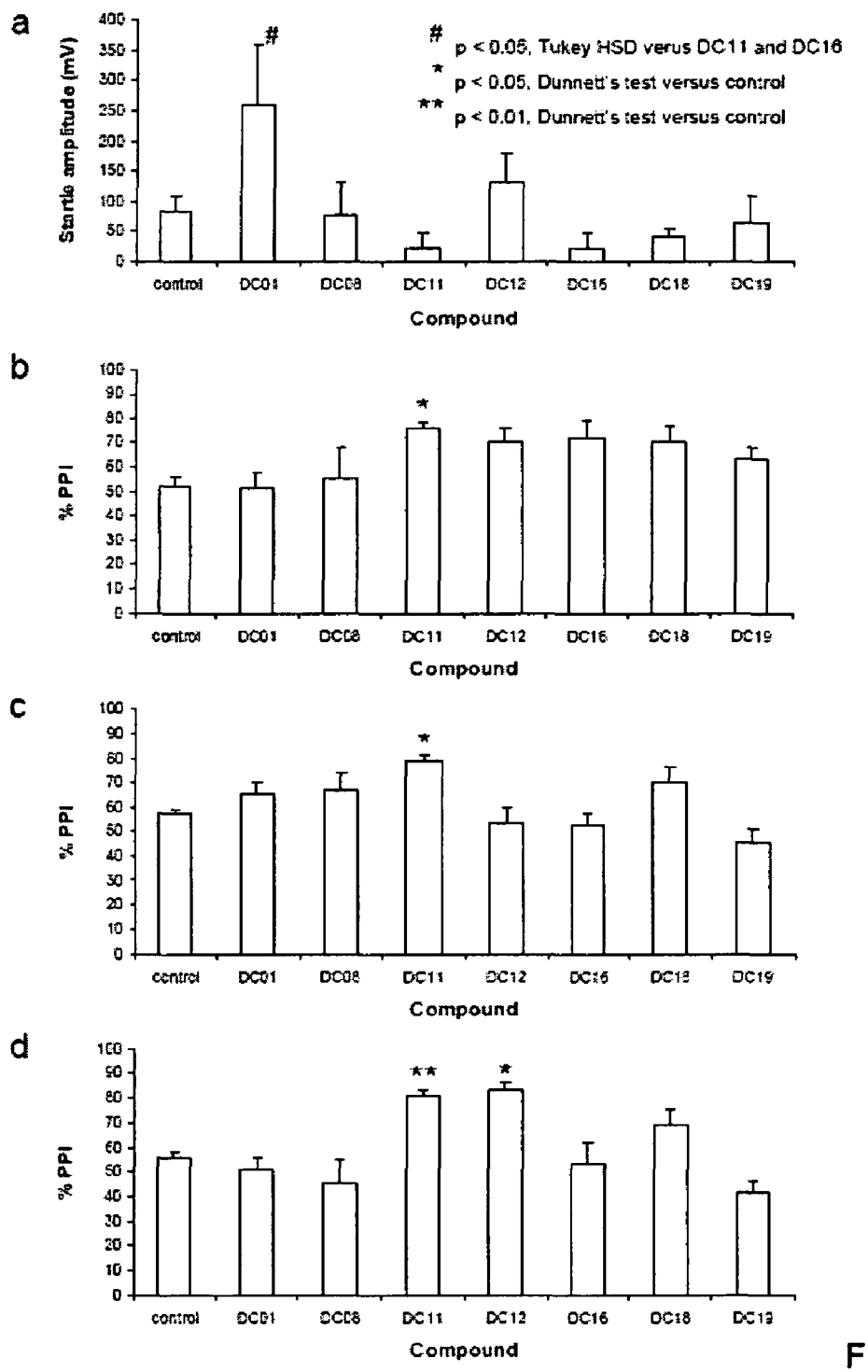
FIG. 2
(a) Graphical representation of startle amplitude data from ckr mouse screening test.
(b) Graphical representation of PPI (pre-pulse inhibition) data from ckr mouse screening test.
(c) Graphical representation of PPI data from ckr mouse screening test.
(d) Graphical representation of PPI data from ckr mouse screening test.

An ANOVA analysis of the ckr screening data shown in FIGS. 1 and 2 indicates that DC16 has biological activity as an agent to treat CNS disorders.

From the teachings of the present invention, those skilled in the art will recognize that various modifications and changes may be made without departing from the spirit of the invention. Such modifications are intended to be with the scope of the present invention.

The invention claimed is:

1. A compound having the following structure:

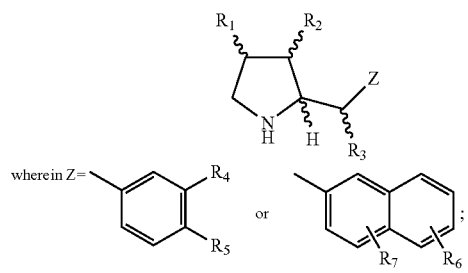

wherein $R_1$ and $R_2$ are selected from H, ORx, C(O)ORx or C(O)N(Rx)Rx and Rx is independently at each occurrence, a hydrogen, alkyl or alkenyl group comprising chains of 8 carbons or less, aryl group, or amino group, further if $R_1$ is ORx, C(O)ORx or C(O)N(Rx)Rx then $R_2$ is H or if $R_2$ is ORx, C(O)ORx or C(O)N(Rx)Rx then $R_1$ is H, and if $R_1$ is H, $R_2$ is not H;

wherein $R_3$=CO$_2$Ry, CH$_2$ORy and Ry is a hydrogen, alkyl or alkenyl group comprising chains of 8 carbons or less, aryl group, or amino group;

wherein $R_4$=alkyl, aryl, alkenyl, alkoxy, halo, nitro, cyano, keto, amino, or carboxylate; and, wherein $R_5$=alkyl, aryl, alkenyl, alkoxy, halo, nitro, cyano, keto, amino, or carboxylate;

wherein $R_6$=hydrogen, alkyl, aryl, alkenyl, alkoxy, halo, nitro, cyano, keto, amino, or carboxylate; and, wherein $R_7$=hydrogen, alkyl, aryl, alkenyl, alkoxy, halo, nitro, cyano, keto, amino, or carboxylate;

a stereoisomer thereof, or a racemic mixture of the compound and the enantiomer of the compound or a pharmaceutically useful salt thereof.

2. The compound of claim 1, wherein Z is a 2-naphthyl group.

3. The compound of claim 1, wherein the stereoisomer is:

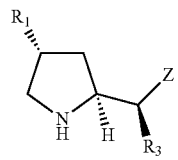

or its enantiomer.

4. The compound of claim 1, wherein the stereoisomer is:

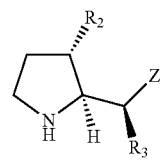

or its enantiomer.

5. The compound of claim 1, wherein the structure of the compound is:

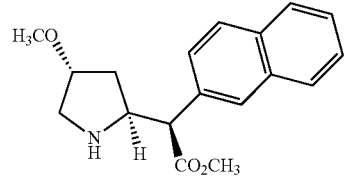

or its enantiomer.

6. The compound of claim 1, wherein the structure of the compound is:

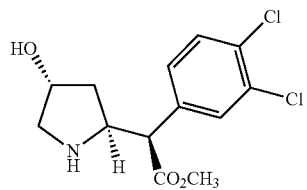

or its enantiomer.

7. The compound of claim 1, wherein the structure of the compound is:

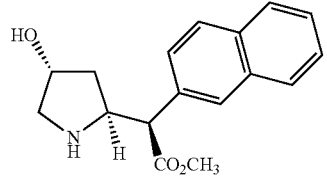

or its enantiomer.

8. The compound of claim 1, wherein the structure of the compound is:

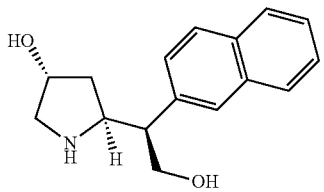

or its enantiomer.

9. The compound of claim 1, wherein the structure of the compound is:

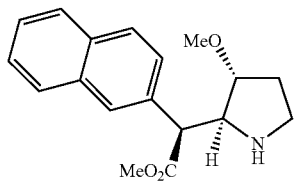

or its enantiomer.

10. The compound of claim 1, wherein the compound is a pharmaceutically useful salt.

11. The compound of claim 1, wherein the compound is the hydrochloride salt.

12. A composition comprising a compound having the following structure:

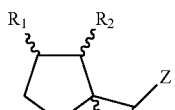

wherein $R_1$ and $R_2$ are selected from H, ORx, C(O)ORx or C(O)N(Rx)Rx and Rx is independently at each occurrence, a hydrogen, alkyl or alkenyl group comprising chains of 8 carbons or less, aryl group, or amino group, further if $R_1$ is ORx, C(O)ORx or C(O)N(Rx)Rx then $R_2$ is H or if $R_2$ is ORx, C(O)ORx or C(O)N(Rx)Rx then $R_1$ is H, and if $R_1$ is H, $R_2$ is not H;
wherein $R_3$=CO$_2$Ry, CH$_2$ORy and Ry is a hydrogen, alkyl or alkenyl group comprising chains of 8 carbons or less, aryl group, or amino group;
wherein $R_4$=alkyl, aryl, alkenyl, alkoxy, halo, nitro, cyano, keto, amino, or carboxylate; and,
wherein $R_5$=alkyl, aryl, alkenyl, alkoxy, halo, nitro, cyano, keto, amino, or carboxylate;
wherein $R_6$=hydrogen, alkyl, aryl, alkenyl, alkoxy, halo, nitro, cyano, keto, amino, or carboxylate; and,
wherein $R_7$=hydrogen, alkyl, aryl, alkenyl, alkoxy, halo, nitro, cyano, keto, amino, or carboxylate;
a stereoisomer thereof, or a racemic mixture of the compound and the enantiomer of the compound or a pharmaceutically useful salt thereof.

13. A composition as in claim 12 wherein Z is a 2-naphthyl group.

14. A composition as in claim 12 wherein the stereoisomer is:

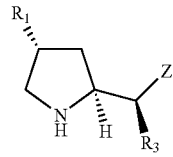

or its enantiomer.

15. A composition as in claim 12 wherein the stereoisomer is:

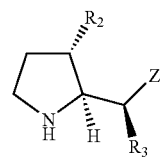

or its enantiomer.

16. A composition as in claim 12 wherein the structure of the compound is:

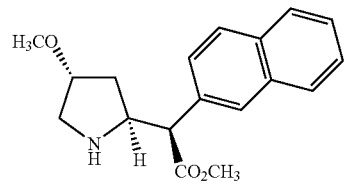

or its enantiomer.

17. A composition as in claim 12 wherein the structure of the compound is:

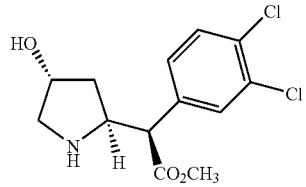

or its enantiomer.

18. A composition as in claim 12 wherein the structure of the compound is:

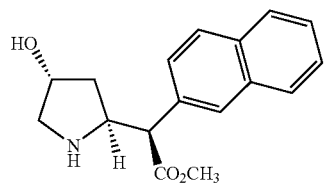

or its enantiomer.

19. A composition as in claim 12 wherein the structure of the compound is:

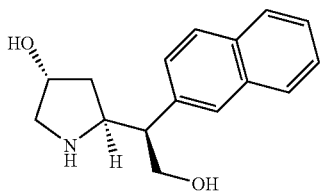

or its enantiomer.

20. A composition as in claim 12 wherein the structure of the compound is:

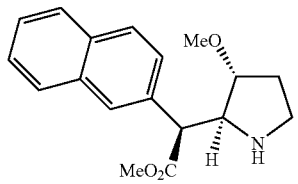

or its enantiomer.

21. A composition as in claim 12 wherein the compound is a pharmaceutically useful salt.

22. A composition as in claim 12 wherein the compound is the hydrochloride salt.

23. A method for alleviating one or more symptoms of a neuropsychiatric disorder in an individual comprising administering to the individual a composition of claim 12 in an amount effective to alleviate the symptoms of the neuropsychiatric disorder.

24. The method of claim 23 wherein the structure of the compound is:

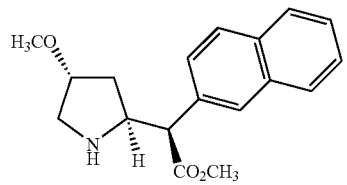

or its enantiomer.

25. The method of claim 23 wherein the structure of the compound is:

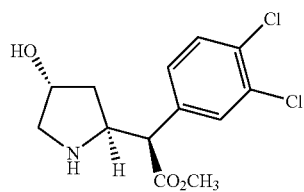

or its enantiomer.

26. The method of claim 23 wherein the structure of the compound is:

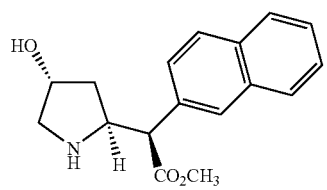

or its enantiomer.

27. The method of claim 23 wherein the structure of the compound is:

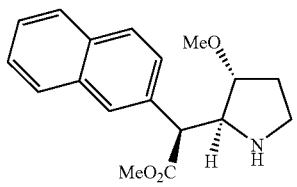

or its enantiomer.

28. The method of claim 23 wherein the compound is a pharmaceutically useful salt.

29. The method of claim 28 wherein the compound is the hydrochloride salt.

* * * * *